(12) United States Patent
Choi et al.

(10) Patent No.: US 10,716,866 B2
(45) Date of Patent: Jul. 21, 2020

(54) PHARMACEUTICAL COMPOSITION COMPRISING AIMP2-DX2 FOR PREVENTING OR TREATING NEURONAL DISEASES AND USE THEREOF

(71) Applicant: Generoath Co., Ltd, Seoul (KR)

(72) Inventors: Jin Woo Choi, Seoul (KR); Dong Uk Lee, Seoul (KR); Ki Hwan Eum, Ansan-si (KR)

(73) Assignee: GENEROATH CO., LTD, Seoul (KR)

( * ) Notice: Subject to any disclaimer, the term of this patent is extended or adjusted under 35 U.S.C. 154(b) by 0 days.

(21) Appl. No.: 15/940,236

(22) Filed: Mar. 29, 2018

(65) Prior Publication Data

US 2019/0298858 A1     Oct. 3, 2019

(51) Int. Cl.

| | |
|---|---|
| *A61K 48/00* | (2006.01) |
| *C12N 15/85* | (2006.01) |
| *A61K 45/06* | (2006.01) |
| *A61P 35/00* | (2006.01) |

(52) U.S. Cl.
CPC ............ *A61K 48/005* (2013.01); *A61K 45/06* (2013.01); *A61P 35/00* (2018.01); *C12N 15/85* (2013.01); *C12N 2750/14141* (2013.01)

(58) Field of Classification Search
CPC ....................... A61K 48/0005; A61K 48/0075
See application file for complete search history.

(56) References Cited

U.S. PATENT DOCUMENTS 8,003,780 B2     8/2011     Kim et al.

FOREIGN PATENT DOCUMENTS

| KR | 10-1067816 B1 | 9/2011 |
|---|---|---|
| KR | 101749138 B1 | 6/2017 |
| KR | 1020170105763 A | 9/2017 |

OTHER PUBLICATIONS

Cappella et al. International Journal of Molecular Science 20,4388: doi.org/10.3390/ijms20184388. pp. 1-21 (Year: 2019).*
KR101067816B1, English translation, printout from google patents on Sep. 19, 2019. pp. 1-15.*
Hitti et al. Parkinsonisn and Related Disorders. 2019. //dio.org/10.1016/j.parkrekdis.2019.07.018.pp. 1-9 (Year: 2019).*
Choong et al. Expert Opinion on Biological Therapy 16(2)143-159, 2016 (Year: 2016).*
Moss, R. B., et al., Repeated Aerosolized AAV-CFTR for Treatment of Cystic Fibrosis: A Randomized Placebo-Controlled Phase 2B Trial, Human Gene Therapy, Aug. 2007, 726-732.
Wu, Z., et al, Optimization of Self-complementary AAV Vectors for Liver-directed Expression Results in Sustained Correction of Hemophilia B at Low Vector Dose, Molecular Therapy, Feb 2008, 281-289, vol. 16, No. 2, The American Society of Gene Therapy.
Sabatino, D. E., et al, Persistent Expression of hF.IX After Tolerance Induction by in Utero or Neonatal Administration of AAV-1-F.IX in Hemophilia B Mice, Molecular Therapy, Sep. 2007, 1677-1685, vol. 15 No. 9.
Wiwanitkit, V., Functions of AAV-CMV-F.IX and AAV-EF1alpha-F.IX in Gene Therapy for Hemophilia B, Human Gene Therapy, Feb. 2007, 89-92.
McPhee, W., et al., Immune responses to AAV in a phase I study for Canavan disease, The Journal of Gene Medicine, 2006, 577-588.
Li, C. et al., Adeno-associated virus vectors: potential applications for cancer gene therapy, Cancer Gene Therapy, 2005, 913-925.
Hacker, U. T., et al., Adeno-associated virus serotypes 1 to 5 mediated tumor cell directed gene transfer and Improvement of transduction efficiency, The Journal of Gene Medicine, 2005, 1429-1438.
Puhlmann M. et al., Thymidine Kinase-Deleted Vaccinia Virus Expressing Purine Nucleoside Phosphorylase as a Vector for Tumor-Directed Gene Therapy, Human Gene Therapy, Mar. 1, 1999, 649-657.
Anthony A.G. Ridgway, Chapter 24—Mammalian Expression Vectors, Elsevier Ltd.,1988, 467-492.
Coupar et al., A general method for the construction of recombinant vaccinia viruses expressing multiple foreign genes, Gene, 1988, 1-10.
Wang et al., Feline immunodeficiency virus vectors persistently transduce nondividing airway epithelia and correct the cystic fibrosis defect, The Journal of Clinical Investigation, Sep. 10, 1999, 55-62.
Chamber R., et al., Comparison of genetically engineered herpes simplex viruses for the treatment of brain tumors in a scid mouse model of human malignant glioma, Proc. Natl. Ac.ad. Sci. USA, Feb. 1995, pp. 1411-1415.
Nicolau et al., Dependence of The Transfer Efficiency Upon the Type of Liposomes Used and The Host Cell Cycle Stage, Biochimica et Biophysica Acta, 1982, 185-190.
Nicolau et al., Liposomes as Carriers for in Vivo Gene Transfer and Expression, Methods in Enzymology, 1987, 157-176.
Capecchi, M.R., High Efficiency Transformation by Direct Microinjection of DNA into Cultured Mammalian Cells, Cell, Nov. 1980, 479-488.
Harland et al., Translation of mRNA Injected into Xenopus Oocytes is Specifically Inhibited by Antisense RNA, The Journal of Cell Biology, Sep. 1, 1985, 1094-1099.

(Continued)

Primary Examiner — Marcia S Noble
(74) *Attorney, Agent, or Firm* — Potomac Law Group, PLLC

(57) ABSTRACT

Provided is a pharmaceutical composition for preventing or treating neuronal diseases comprising, as an active ingredient, an exon 2-deleted AIMP2 variant (AIMP2-DX2) gene or a vector comprising the gene, and a method for treating neuronal diseases in animals other than humans, comprising administering the same to a subject in need of treatment. The pharmaceutical composition comprising, as an active ingredient, a AIMP2-DX2 gene or a vector comprising the gene has the effects of apoptosis inhibition, dyskinesia amelioration and oxidative stress inhibition and thus can be widely used for preventing and treating neuronal diseases such as Parkinson's disease and amyotrophic lateral sclerosis.

9 Claims, 4 Drawing Sheets

Specification includes a Sequence Listing.

(56) References Cited

OTHER PUBLICATIONS

Graham, F.L. et al., A New Technique for the Assay of Infectivity of Human Adenovirus 5 DNA, Virology, 1973, 456-467.
Chen et al., High-Efficiency Transformation of Mammalian Cells by Plasmid DNA, Molecular and Cellular Biology, Aug. 1987, p. 2745-2752.
Neumann, E. et al., Gene transfer into mouse lyoma cells by electroporation in high electric fields, The EMBO Journal, 1982, pp. 841-845.
Tur-Kaspa et al., Use of Electroporation to Introduce Biologically Active Foreign Genes into Primary Rat Hepatocytes, Molecular and Cellular Biology, Feb. 1986, p. 716-718.
Wong, T.K. et al., Appearance of beta-lactamase activity in animal cells upon liposome-mediated gene transfer, Gene, 1980, 87-94.
T. Venkat Gopal., Gene Transfer Method for Transient Gene Expression, Stable Transformation, and Cotransformation of Suspension Cell Cultures, Molecular and Cellular Biology, May 1985, p. 1188-1190.
Jin Woo Choi et al. "Splicing variant of AIMP2 as an effective target against chemoresistant ovarian cancer". Journal of Molecular Cell Biology (2012), 4, pp. 164-173.
Choi, J. et al., "AIMP2 promotes TNFa-dependent apoptosis via ubiquitin-mediated degradation of TRAF2," Journal of Cell Science, 2009, vol. 122, p. 2710-2715, The Company of Biologists, United Kingdom.
Kam, T-I. et al., "Poly(ADP-ribose) drives pathologic a-synuclein neurodegeneration in Parkinson's disease," Science, Nov. 2018, vol. 362, p. 1-12, American Association for the Advancement of Science, Washington DC.
Kim, D., et al., "Interaction of two translational components, lysyl-tRNA synthetase and p40/37LRP, in plasma membrane promotes laminin-dependent cell migration," The FASEB Journal—Research Communication, 2017, vol. 26:10, p. 4142-4159, Federation of American Societies for Experimental Biology, Bethesda, MD.
Ko, H. et al., "Phosphorylation by the c-Abl protein tyrosine kinase inhibits parkin's ubiquitination and protective function," Proceedings of the National Academy of Sciences of the United States of America, 2010, vol. 107:38, p. 16691-16696, Washington DC.
Lee, Y. et al., "Parthanatos mediates AIMP2-activated age-dependent dopaminergic neuronal loss," Nature Neuroscience, 2013, vol. 16, p. 1-12, Springer Nature Limited, United Kingdom.

* cited by examiner

SEQUENCE LISTING

```
<160> NUMBER OF SEQ ID NOS: 4

<210> SEQ ID NO 1
<211> LENGTH: 756
<212> TYPE: DNA
<213> ORGANISM: Homo sapiens

<400> SEQUENCE: 1
atgccgatgt accaggtaaa gccctatcac gggggcggcg cgcctctccg tgtggagctt      60
cccacctgca tgtaccggct ccccaacgtg cacggcagga gctacggccc agcgccgggc     120
gctggccacg tgcaggatta cggggcgctg aaagacatcg tgatcaacgc aaacccggcc     180
tcccctcccc tctccctgct tgtgctgcac aggctgctct gtgagcactt cagggtcctg     240
tccacggtgc acacgcactc ctcggtcaag agcgtgcctg aaaaccttct caagtgcttt     300
ggagaacaga ataaaaaaca gccccgccaa gactatcagc tgggattcac tttaatttgg     360
aagaatgtgc cgaagacgca gatgaaattc agcatccaga cgatgtgccc catcgaaggc     420
gaagggaaca ttgcacgttt cttgttctct ctgtttggcc agaagcataa tgctgtcaac     480
gcaaccctta tagatagctg ggtagatatt gcgattttc agttaaaaga gggaagcagt     540
aaagaaaaag ccgctgtttt ccgctccatg aactctgctc ttgggaagag cccttggctc     600
gctgggaatg aactcaccgt agcagacgtg gtgctgtggt ctgtactcca gcagatcgga     660
ggctgcagtg tgacagtgcc agccaatgtg cagaggtgga tgaggtcttg tgaaaacctg     720 gctccttta acacggccct caagctcctt aagtga                                756

<210> SEQ ID NO 2
<211> LENGTH: 251
<212> TYPE: PRT
<213> ORGANISM: Homo sapiens

<400> SEQUENCE: 2

Met Pro Met Tyr Gln Val Lys Pro Tyr His Gly Gly Ala Pro Leu
1               5                   10                  15

Arg Val Glu Leu Pro Thr Cys Met Tyr Arg Leu Pro Asn Val His Gly
                20                  25                  30

Arg Ser Tyr Gly Pro Ala Pro Gly Ala Gly His Val Gln Asp Tyr Gly
            35                  40                  45

Ala Leu Lys Asp Ile Val Ile Asn Ala Asn Pro Ala Ser Pro Pro Leu
        50                  55                  60

Ser Leu Leu Val Leu His Arg Leu Leu Cys Glu His Phe Arg Val Leu
65                  70                  75                  80

Ser Thr Val His Thr His Ser Ser Val Lys Ser Val Pro Glu Asn Leu
                85                  90                  95
```

| | | | | | | | | | | | | |
|---|---|---|---|---|---|---|---|---|---|---|---|---|
|Leu|Lys|Cys|Phe|Gly|Glu|Gln|Asn|Lys|Lys|Gln|Pro|Arg|Gln|Asp|Tyr|
| | | |100| | | |105| | | |110| | | | |

```
Leu Lys Cys Phe Gly Glu Gln Asn Lys Lys Gln Pro Arg Gln Asp Tyr
                100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
        180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
210                 215                 220

Thr Val Pro Ala Asn Val Gln Arg Trp Met Arg Ser Cys Glu Asn Leu
225                 230                 235                 240

Ala Pro Phe Asn Thr Ala Leu Lys Leu Leu Lys
                245                 250
```

<210> SEQ ID NO 3
<211> LENGTH: 936
<212> TYPE: DNA
<213> ORGANISM: Homo sapiens

<400> SEQUENCE: 3

```
atgccgatgt accaggtaaa gccctatcac gggggcggcg cgcctctccg tgtggagctt      60
cccacctgca tgtaccggct ccccaacgtg cacggcagga gctacggccc agcgccgggc     120
gctggccacg tgcaggaaga gtctaacctg tctctgcaag ctcttgagtc cgccaagat      180
gatattttaa acgtctgta tgagttgaaa gctgcagttg atggcctctc caagatgatt     240
caaacaccag atgcagactt ggatgtaacc aacataatcc aagcggatga gcccacgact     300
ttaaccacca tgcgctgga cttgaattca gtgcttggga aggattacgg ggcgctgaaa     360
gacatcgtga tcaacgcaaa cccggcctcc cctcccctct ccctgcttgt gctgcacagg     420
ctgctctgtg agcacttcag ggtcctgtcc acggtgcaca cgcactcctc ggtcaagagc     480
gtgcctgaaa accttctcaa gtgctttgga gaacagaata aaaaacagcc ccgccaagac     540
tatcagctgg gattcacttt aatttggaag aatgtgccga gacgcagat gaaattcagc     600
atccagacga tgtgccccat cgaaggcgaa gggaacattg cacgtttctt gttctctctg     660
tttggccaga agcataatgc tgtcaacgca acccttatag atagctgggt agatattgcg     720
atttttcagt taaagagggg aagcagtaaa gaaaaagccg ctgttttccg ctccatgaac     780
tctgctcttg ggaagagccc ttggctcgct gggaatgaac tcaccgtagc agacgtggtg     840
ctgtggtctg tactccagca gatcggaggc tgcagtgtga cagtgccagc caatgtgcag     900
aggtggatga ggtcttgtga aaacctggct cctttt                                936
```

<210> SEQ ID NO 4
<211> LENGTH: 207
<212> TYPE: DNA
<213> ORGANISM: Homo sapiens

<400> SEQUENCE: 4

```
gaagagtcta acctgtctct gcaagctctt gagtcccgcc aagatgatat tttaaaacgt      60
```

```
ctgtatgagt tgaaagctgc agttgatggc ctctccaaga tgattcaaac accagatgca      120
gacttggatg taaccaacat aatccaagcg gatgagccca cgactttaac caccaatgcg      180
ctggacttga attcagtgct tgggaag                                          207
```

PHARMACEUTICAL COMPOSITION COMPRISING AIMP2-DX2 FOR PREVENTING OR TREATING NEURONAL DISEASES AND USE THEREOF

REFERENCE TO AN ELECTRONIC SEQUENCE LISTING

The contents of the electronic sequence listing (8-PK0172480-SequenceListing.txt; Size: 5,257 bytes; and Date of Creation: Mar. 29, 2018) is herein incorporated by reference in its entirety.

BACKGROUND OF THE INVENTION

Field of the Invention

The present invention relates to a pharmaceutical composition for preventing or treating neuronal diseases comprising, as an active ingredient, an exon 2-deleted AIMP2 variant (AIMP2-DX2) polypeptide or a viral vector comprising the AIMP2-DX2, more specifically, an adeno-associated virus (AAV) carrying AIMP2-DX2, and a method for treating neuronal diseases in animals other than humans, comprising administering the pharmaceutical composition to a subject in need of treatment.

Description of the Related Art

Neurons continue to undergo apoptosis during development and synaptic reconstruction, and apoptosis caused by stress and cytotoxic drugs is a major cause of degenerative brain diseases. Among them, oxidative stress is known to have a significant connection with the cause of degenerative brain diseases such as Parkinson's disease, stress, aging, stroke and Huntington's disease. Recent studies showed that chronic stress and oxidative stress cause oxidative stress to increase apoptosis in the hypothalamo-pituitary-adrenocortical system, hippocampus, striatum, substantia nigra and frontal cortex areas, and reduce neurons and growth factors to cause Parkinson's disease, stress, aging, stroke, and Huntington's disease.

Particularly, free radicals from oxygen are known as a major cause of tissue damage. Oxygen radicals associated with neurotoxicity include hydrogen peroxide, a hydrogen peroxide anion, a hydroxyl group, and the like. Among them, hydrogen peroxide is known as the most important substance as a precursor of a highly reactive free radical and is likely to cause apoptosis in the central nervous system.

If brain neurons undergo oxidative stress, reactive oxygen species (ROS) are triggered to cause cytochrome C release and caspase-3 activation in mitochondria, resulting in apoptosis. In addition, ROS results in the activation of glutamate, particularly the NMDA receptor, which increases $Ca^{2+}$ ions by the metabotrophic cascade, and the increase in intracellular $Ca^{2+}$ associated with ROS also results in caspase-2 activation, causing DNA damage.

Among neuronal diseases, Parkinson's disease is known to occur due to gradual loss of dopaminergic neurons in the substantia nigra of the brain. It is a chronic, progressive degenerative disorder of the nervous system characterized by resting tremor, stiffness, bradycinesia and postural instability. In addition to these typical abnormal movement symptoms, Parkinson's disease may involve autonomic nervous system symptoms, neuropsychiatric symptoms, cognitive dysfunction, sleep disorders, pain, fatigue, and olfactory disorders. The cause of Parkinson's disease has not yet been elucidated. Currently, a common treatment for Parkinson's disease is a levodopa therapy based on levodopa, which is a dopamine precursor. In recent years, levodopa combined with an enzyme for preventing levodopa from decomposing before it reaches the brain has been mainly used. However, in the course of treatment with the drug, various dyskinesias associated with the drug or resulting from disease progress are observed. In general, a dopamine agonist, a lyase inhibitor or the like is used in combination with the drug to treat them. Some of the symptoms of Parkinson's disease do not respond to dopamine drugs. When these non-motor symptoms occur, an allopathic treatment to alleviate the symptoms concerned is used. Meanwhile, depression is the most common mood disorder linked to Parkinson's disease, for which a serotonin reuptake inhibitor (SSRI), a tricyclic antidepressant and the like are administered. Recently, a surgical treatment for typical Parkinson's disease has been developed and implemented which alleviates the symptoms of Parkinson's disease by applying high-frequency electrical stimulation to the subthalamic nucleus and the like deep in the brain. However, a therapeutic agent capable of preventing or completely treating Parkinson's disease has not yet been developed. Most of the treatments are to alleviate its symptoms through medication or rely on surgical techniques that provide electrical stimulation as mentioned above.

Among neuronal diseases, amyotrophic lateral sclerosis is a disease that selectively kills motor neurons. It is a fatal disease characterized by gradual destruction of upper motor neurons of the cerebral cortex (cortex) and the lower motor neurons of the brain stem and spinal cord. The clinical symptoms start with gradually worsening weakness and atrophy of the limbs, and as the disease progresses, the respiratory muscles are paralyzed, leading to death within a few years. The cause of amyotrophic lateral sclerosis has not yet been elucidated. Several drugs are under development based on the pathogenesis principle, progress and the like of amyotrophic lateral sclerosis, but their efficacy has not been clearly established. The only currently approved drug, riluzole, has the effect of increasing the survival period by about several months. However, it has not yet proven effective in improving quality of life or restoring muscular strength. Thus, currently, there is no treatment for amyotrophic lateral sclerosis, and therefore it is necessary to develop an auxiliary or main treatment for amyotrophic lateral sclerosis, a major rare disease.

AIMP2-DX2 is an alternative splice variant of the tumor suppressor AIMP2, which is associated with apoptosis in many ways. It is known to inhibit apoptosis by suppressing the function of AIMP2.

The present inventor is one of the joint inventors of a patent (Patent Literature 4) which relates to a composition for preventing and treating inflammatory diseases comprising an inhibitor of AIMP2-DX2 as an active ingredient, more particularly to a method for screening a drug for preventing or treating inflammatory diseases, comprising screening a composition for preventing and treating inflammatory diseases comprising an inhibitor of AIMP2-DX2 as an active ingredient, a composition for preventing and treating inflammatory diseases comprising an expression vector inhibiting the expression of AIMP2-DX2 and a substance inhibiting the expression of AIMP2-DX2. Patent Literature 4 demonstrated that AIMP2/p38 promotes ubiquitination of TRAF2 to regulate TNF-α-induced apoptosis and that AIMP2-DX2, a splice variant of AIMP2/p38, serves as a competitive inhibitor of AIMP2 to inhibit the ubiquitin of TRAF2 and thus to inhibit TNF-α-induced apoptosis, thereby promoting tumor generation and inhibiting the expression of Cox-2, an inflammation marker.

In addition, AIMP2-DX2 has been previously identified as a lung cancer-inducing factor. In the study, it was found that AIMP2-DX2, which is a variant of AIMP2, is common in cancer cells and interferes with the cancer inhibitory function of AIMP2, thus causing cancer. It was also found that the expression of AIMP2-DX2 in normal cells leads to cell canceration whereas the inhibition of the development of AIMP2-DX2 inhibits the growth of cancer cells, resulting in cancer treatment effects. Also, the study showed through an animal model that inhibition of AIMP2-DX2 targets can lead to the treatment of ovarian cancer that does not respond to conventional anticancer drugs such as Taxol and cisplatin. However, AIMP2-DX2 itself does not have oncogenic ability to transform normal cells.

The inventor of the present invention demonstrated in vitro and in vivo that when AIMP2-DX2, which acts as an antagonist of AIMP2, is inserted into an adeno-associated virus and the resultant is introduced into neurons, it effectively inhibits neuronal apoptosis and thereby completed the present invention.

SUMMARY OF THE INVENTION

The objective of the present invention is to develop a gene therapy which is injected into neurons to achieve excellent effects on the prevention or treatment of neuronal diseases for which there is no cure or even if there is a cure, the effect is insignificant, and thereby to provide an auxiliary or main treatment for rare neuronal diseases such as Parkinson's disease and amyotrophic lateral sclerosis.

The present invention achieves the above objective by providing a pharmaceutical composition for preventing or treating neuronal diseases comprising, as an active ingredient, an exon 2-deleted AIMP2 variant (AIMP2-DX2) gene or a vector comprising the gene.

In one embodiment of the present invention, the exon 2-deleted AIMP2 variant (AIMP2-DX2) gene or the vector comprising the gene has one or more activities selected from the group consisting of apoptosis inhibition, dyskinesia amelioration and oxidative stress inhibition, and thus has the effect of preventing or treating neuronal diseases.

In one embodiment of the invention, the neuronal diseases are selected from the group consisting of Alzheimer's disease, Parkinson's disease, amyotrophic lateral sclerosis, mild cognitive impairment, multi-infarct dementia, frontotemporal dementia, dementia with Lewy bodies, Huntington's disease, neurodegenerative diseases, metabolic brain diseases, depression, epilepsy, multiple sclerosis, corticobasal degeneration, multiple system atrophy, progressive supranuclear palsy, dentatorubropallidoluysian atrophy, spinocerebella ataxia, primary lateral sclerosis, spinal muscular atrophy and stroke, although not limited thereto.

In one embodiment of the invention, a pharmaceutically acceptable carrier, excipient or diluent may be further included.

Also, the present invention may relate to a form in which the exon 2-deleted AIMP2 variant (AIMP2-DX2) gene is carried on a carrier selected from the group consisting of a viral vector, linear DNA and plasmid DNA.

In one embodiment of the present invention, when the carrier is a viral vector, the viral vector may be selected from the group consisting of adeno-associated virus (AAV), adenovirus, lentivirus, retrovirus, vaccinia virus, and herpes simplex virus.

Also, the present invention achieved the above objective by providing a method for preventing or treating neuronal diseases in a subject, comprising administering a pharmaceutical composition comprising, as an active ingredient, an exon 2-deleted AIMP2 variant (AIMP2-DX2) gene or a vector comprising the gene to an animal subject in need thereof other than a human.

In one embodiment of the present invention, the administration may be performed by introducing an exon 2-deleted AIMP2 variant (AIMP2-DX2) gene or a vector comprising the gene into cells by a method selected from the group consisting of a chemical method, a physical method, conjugation by using a liposome, a method of using a receptor, and a method of using virus.

DETAILED DESCRIPTION OF THE PREFERRED EMBODIMENTS

Figure 1:
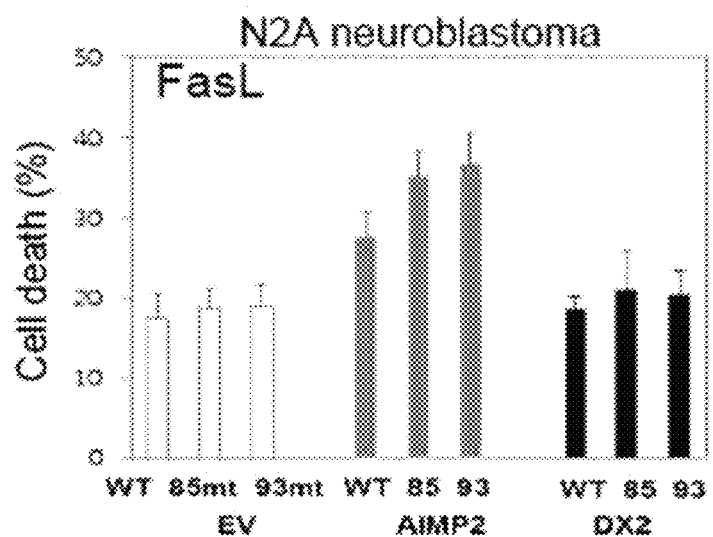
FIG. 1 is a graph showing the results of measuring the effect of an AIMP2-DX2 polypeptide and the control group on inflammatory cytokine-induced apoptosis, in cell groups produced by introducing each of an AIMP2 gene and a DX2 gene into N2A cells transfected with each of WT and 85 and 93 mutants.
Figure 2:
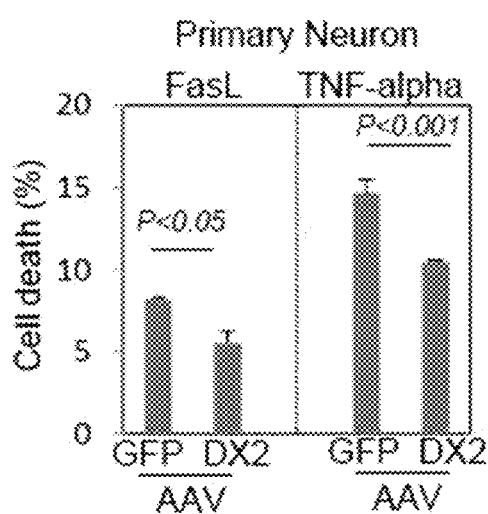
FIG. 2 is a graph showing the results of measuring the effect of AAV-DX2 on apoptosis of primary neurons.
Figure 3:
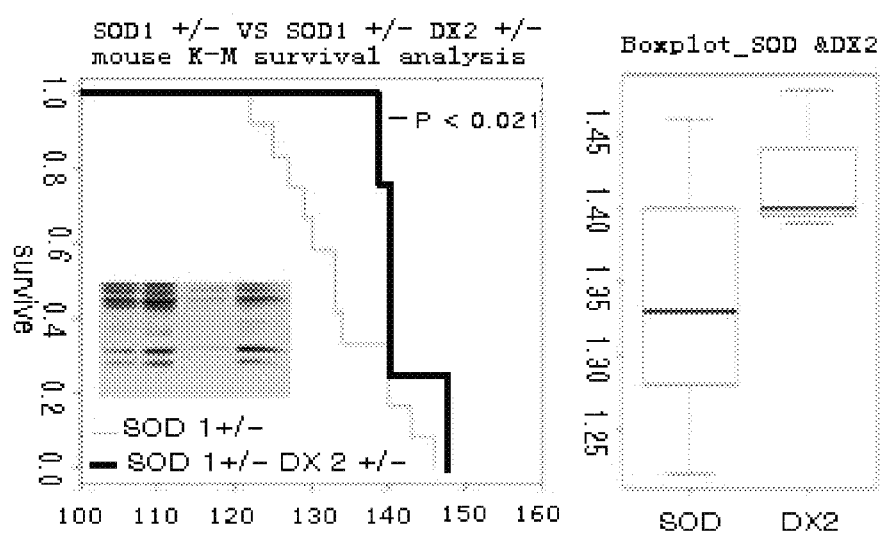
FIG. 3 is a graph showing the results of experiments on how much longer a DX2-SOD1 mouse survives than a SOD mouse.
Figure 4:
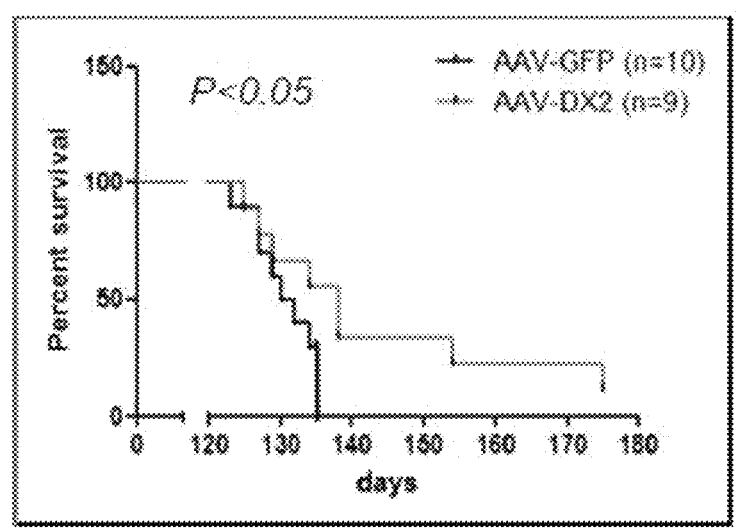
FIG. 4 is a graph showing the results of experiments on the effect of AAV-DX2 on the prolongation of survival period of an ALS mouse.
Figure 5:
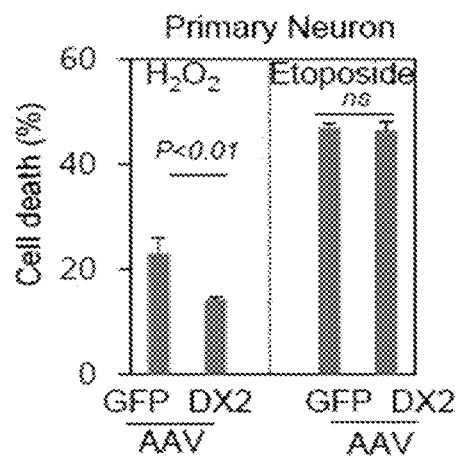
FIG. 5 is a graph showing the results of experiments on the effect of AAV-DX2 on apoptosis of a PD mouse.
Figure 6:
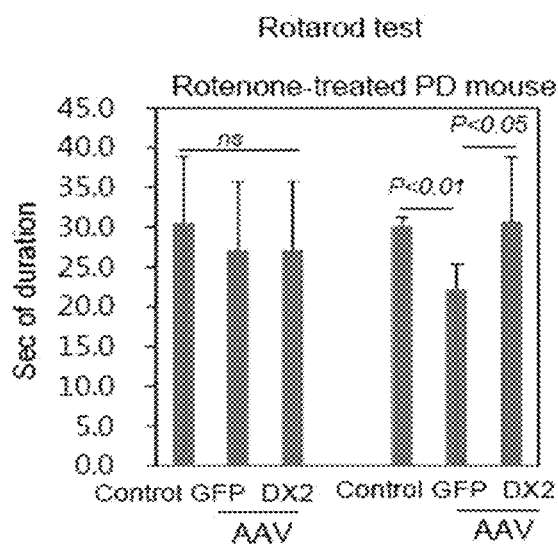
FIG. 6 is a graph showing the results of a rotarod test.
Figure 7:
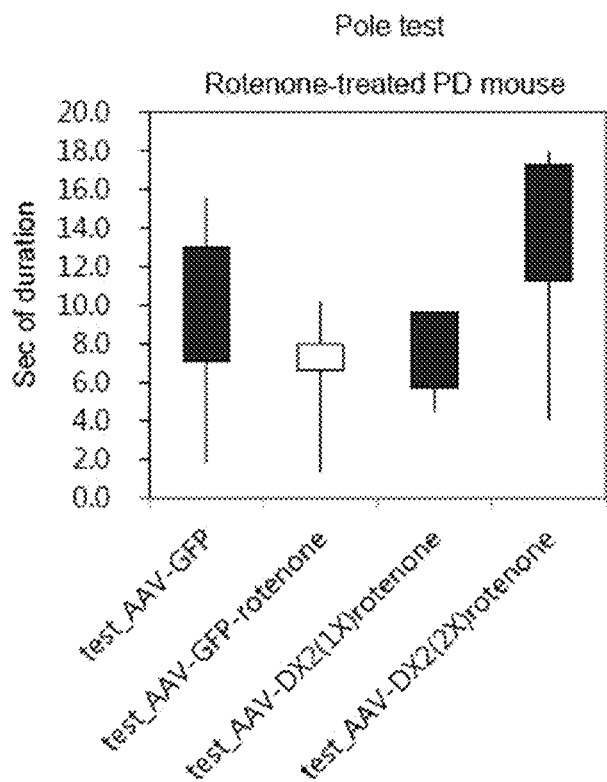
FIG. 7 is a graph showing the results of a pole test.
Figure 8:
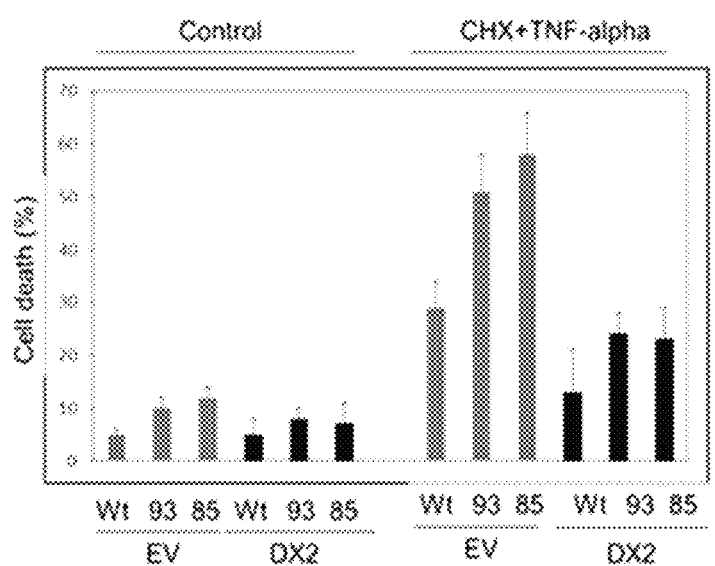
FIG. 8 is a graph showing the results of measuring the degree of apoptosis of cells treated with and without cycloheximide and TNF-alpha, in cell groups produced by introducing a DX2 gene into N2A cells transfected with each of WT and 85 and 93 mutants

The present invention relates to a pharmaceutical composition for preventing or treating neuronal diseases comprising, as an active ingredient, an exon 2-deleted AIMP2 variant (AIMP2-DX2) gene or a vector comprising the gene.

The AIMP2-DX2 polypeptide of the present invention is a splice variant of AIMP2 (SEQ ID NO: 3), in which the second exon (SEQ ID NO: 4) of AIMP2 is omitted. The amino acid sequence thereof is described in Korean Patent No. 1,067,816. Specifically, the AIMP2-DX2 gene has a base sequence set forth in SEQ ID NO: 1, and the AIMP2-DX2 polypeptide has an amino acid sequence set forth in SEQ ID NO: 2.

Experimental results showed that the AIMP2-DX2 polypeptide effectively inhibits inflammatory cytokine-induced apoptosis.

The expression of the exon 2-deleted AIMP2 splice variant in cervical carcinoma (BI259092) and muscle rhabdomyosarcoma (BI115365) was reported in the EST database, which is provided below.

In one embodiment of the present invention, the exon 2-deleted AIMP2 variant (AIMP2-DX2) gene or the vector comprising the gene has one or more activities selected from the group consisting of apoptosis inhibition, dyskinesia amelioration and oxidative stress inhibition, and thus has the effect of preventing or treating neuronal diseases.

In one aspect of the invention, the neuronal diseases are selected from the group consisting of Alzheimer's disease, Parkinson's disease, amyotrophic lateral sclerosis, mild cognitive impairment, multi-infarct dementia, frontotemporal dementia, dementia with Lewy bodies, Huntington's disease, neurodegenerative diseases, metabolic brain diseases, depression, epilepsy, multiple sclerosis, corticobasal degeneration, multiple system atrophy, progressive supranuclear palsy, dentatorubropallidoluysian atrophy, spinocerebella ataxia, primary lateral sclerosis, spinal muscular atrophy and stroke, although not limited thereto.

In one aspect of the invention, the vector may be one or more selected from the group consisting of a viral vector, linear DNA and plasmid DNA.

Gene therapy is classified into two types: in vivo and ex vivo. In in vivo gene therapy, a therapeutic gene is injected into the body directly. In ex vivo gene therapy, target cells are first cultured in vitro, a gene is introduced into these cells, and then the thus obtained, genetically modified cells are injected into the body. Currently, ex vivo gene therapy is used more often than in vivo gene therapy in gene therapy researches.

Gene transfer technology can be largely classified into: a method of using virus as a carrier, a method of using a plasmid, a non-viral method of using a synthetic phospholipid, a synthetic cationic polymer or the like, and physical methods such as electroporation, which introduces a gene by applying transient electrical stimulation to a cell membrane.

Among the above transfer technologies, a method of using a virus carrier is considered to be preferable for gene therapy, because the transfer of a genetic factor can be efficiently made with a vector with the loss of a portion or whole of replicative ability which has a gene substituted with a therapeutic gene.

In one aspect of the present invention, when a viral vector is used, the viral vector may be a recombinant virus using a viral vector selected from the group consisting of adeno-associated virus (AAV), adenovirus, lentivirus, retrovirus, vaccinia virus, and herpes simplex virus.

As used herein, the term "viral vector" refers to a viral vector capable of transferring a therapeutic gene or a genetic material to a desired cell, tissue and/or organ.

Examples of viruses used as the virus carrier or viral vector include RNA virus vectors (retrovirus vectors, lentivirus vectors, and the like), and DNA virus vectors (adenovirus vectors, adeno-associated virus vectors, and the like). In addition, the examples include herpes simplex viral vectors and alpha viral vectors.

A retrovirus is widely used as a gene transfer vector because it can insert its gene into the host's genome, carry large quantities of foreign genetic material and infect a broad spectrum of cells.

The retrovirus can be integrated into the host cell's genome. When integrated, it can suppress normal cells' functions although it is harmless to the human body. It can infect a variety of cells and easily proliferates. It can accommodate a foreign gene of about 1 to 7 kb and produce a replication defective virus. However, the retrovirus has disadvantages that it has difficulty in infecting cells after mitosis and transferring a gene in vivo and that somatic tissues should always be proliferated in vitro. In addition, the retrovirus can be integrated into proto-oncogenes, which may lead to mutation and necrosis.

An adenovirus has several advantages as a cloning vector. It can be replicated in the nucleus into a medium size and is clinically non-toxic. Even when a foreign gene is inserted, it is stable without rearrangement or loss of a gene. It can transfect eukaryotes and is expressed at a high level in a stable manner even when incorporated into the host cell's chromosome. Cells that cause human hematopoiesis, lymphoma, and myeloma are good host cells for an adenovirus. However, the adenovirus is difficult to proliferate because it is linear DNA. Also, it is not easy to recover the infected virus and the virus infection rate is low. Further, the expression of the transferred gene is most abundant after 1 to 2 weeks, and in some cells, the expression is maintained only for 3 to 4 weeks. What is also problematic is that it has high immunogenicity.

An adeno-associated virus (AAV) has recently been preferred because it has many advantages as a gene therapy without the above-mentioned problems.

The adeno-associated virus (AAV) is also referred to as an adeno-satellite virus. The adeno-associated virus particle is 20 nm in diameter. It is known to be harmless to humans and thus was approved for sale as a gene therapy in Europe.

AAV, which is single-strand provirus, requires a helper virus for replication. The AAV genome is 4,680 bp in size and can be inserted into a specific site of chromosome 19 of infected cells. A transgene is inserted into plasmid DNA linked by two copies of a 145-bp inverted terminal repeat (ITR) sequence and a signal sequence. This gene is transfected with another plasmid DNA expressing AAV rep and cap genes, and adenovirus is added as a helper virus. AAV has advantages that it transfers a gene to a wide range of host cells, has fewer side effects upon repeated administration, and has long gene expression time. Further, it is stable even when the AAV genome is integrated into the chromosome of a host cell, and it does not cause the modification or rearrangement of gene expression in host cells.

The adeno-associated virus is known to have four serotypes. Among the serotypes of many adeno-associated viruses that can be used for the transfer of a desired gene, the most widely studied vector is adeno-associated virus serotype 2, which is currently used for clinical gene transfer for cystic fibrosis [1], hemophilia [2] and Canavan disease [3]. Recently, the potential of recombinant adeno-associated virus (rAAV) has been increasing in cancer gene therapy [4]. The present invention also uses adeno-associated virus serotype 2, and a suitable viral vector can be selected and applied.

Other viral vectors may also be used as the gene transfer system of the present invention. Vectors derived from vaccinia virus [5], lentivirus [6], and herpes simplex virus [7] can also be used as the delivery system.

The gene according to the present invention may also be transferred using a liposome, a nanoparticle carrier, microinjection, electroporation or the like.

Among them, the liposome may be, for example, a liposome, a nanoliposome, a proteoliposome, a ceramide-containing nanoliposome. The liposome is automatically formed by a phospholipid dispersed in an aqueous phase. An example in which a foreign DNA molecule is carried into cells by a liposome is described in Reference Document 8. Reagents such as lipofectamine are often used for transfection of animal cells using a liposome. A liposome containing an exon 2-deleted AIMP2 variant (AIMP2-DX2) gene interacts with cells through a mechanism such as endocytosis, adsorption to cell surfaces or fusion with plasma membrane to transfer the exon 2-deleted AIMP2 variant (AIMP2-DX2) gene into cells.

The gene transfer system may be introduced into cells by various methods known in the art. In case where the gene transfer system is constructed based on a viral vector, it may be introduced according to a virus infection method known in the art. In case where the gene transfer system is a naked recombinant DNA molecule or a plasmid, the gene may be introduced into cells by microinjection [9], calcium phosphate precipitation [10], electroporation [11], liposome-mediated transfection [12], DEAE-dextran treatment [13] and the like. In addition, one of nanoparticles, calcium phosphorus-silicate nanoparticles, calcium phosphate nanoparticles, silicon dioxide nanoparticles, nanocrystalline particles, poly(D-arginine), nano-dendrimers may be used.

In one aspect of the invention, a pharmaceutically acceptable carrier, excipient or diluent may be further included.

The present invention also relates to a method for preventing or treating neuronal diseases in a subject, comprising administering a pharmaceutical composition comprising, as an active ingredient, an exon 2-deleted AIMP2 variant (AIMP2-DX2) gene or a vector comprising the gene to an animal subject in need thereof other than a human.

In one aspect, the present invention relates to a method for preventing or treating neuronal diseases in a subject, comprising administering an adeno-associated virus (AAV) comprising an exon 2-deleted AIMP2 variant (AIMP2-DX2) gene to an animal subject in need thereof other than a human.

In one aspect of the present invention, the administration may be performed by introducing an exon 2-deleted AIMP2 variant (AIMP2-DX2) gene or a vector comprising the gene into cells by a method selected from the group consisting of a chemical method, a physical method, conjugation by using a liposome, and a method of using virus, as described above.

As used herein, the term "animals other than humans" refers to animals such as a pig, a cow, a horse, a sheep, a goat and a dog other than humans having a neuronal disease whose symptoms can be ameliorated by administration of the pharmaceutical composition according to the present invention. It is possible to effectively prevent and treat neuronal diseases by administering the pharmaceutical composition of the present invention to animals other than humans.

The standard recombinant DNA and molecular cloning technology used in the present invention are well known in the art and described in Reference Document 14.

The pharmaceutical composition of the present invention is administered in a pharmaceutically effective amount. As used herein, the term "pharmaceutically effective amount" refers to an amount sufficient to treat diseases, at a reasonable benefit/risk ratio applicable to medical treatment or amelioration. The effective dosage level of the composition may be determined depending on the type of the subject, the severity of the disease, the subject's age and gender, the activity of the drug, sensitivity to the drug, administration time, administration route and excretion rate, the duration of treatment, drugs used in combination with the composition, and other factors known in the medical field.

The pharmaceutical composition of the present invention may be administered as an individual therapeutic agent or in combination with another therapeutic agent. It may be administered sequentially or simultaneously with a conventional therapeutic agent. The pharmaceutical composition of the present invention may be administered singly or multiply. It is important to administer the composition in the minimum amount that can exhibit the maximum effect without causing side effects, in view of all the above-described factors, and this amount can be easily determined by a person skilled in the art. Specifically, it is preferable to administer the pharmaceutical composition of the present invention intrathecally, intracerebrally, or intravenously.

Although the method for treatment according to the present invention is to treat animals other than humans, it does not mean that the method for treatment is not effective in humans. Further, considering that there are human neuronal diseases whose symptoms can be ameliorated by administration of the therapeutic composition according to the present invention, it can be sufficiently used to treat humans.

As used herein, "treating" refers to not only a complete cure of a neuronal disease but also a partial cure, amelioration and alleviation of symptoms due to a neural disease which is caused by application of the pharmaceutical composition of the present invention to a subject having a neuronal disease.

As used herein, the term "preventing" refers to inhibiting the occurrence of the symptoms of a neuronal disorder by applying the pharmaceutical composition of the present invention to a subject with a neuronal disease to inhibit or block symptoms or phenomena such as cognitive disorder, behavioral disorder and brain nerve destruction.

The pharmaceutically acceptable carriers included in the composition of the present invention are those conventionally used for formulation and include, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil.

The pharmaceutical composition of the present invention may further comprise a lubricant, a wetting agent, a sweetening agent, a flavoring agent, an emulsifying agent, a suspending agent, a preservative, and the like in addition to the above ingredients.

As used herein, the term "administering" refers to introducing a predetermined substance into an animal by an appropriate method. The pharmaceutical composition according to the present invention may be administered orally or parenterally through a common route as long as it gets to the target tissue. Also, the therapeutic composition according to the present invention may be administered by any device capable of moving the active ingredient to the target cell.

The preferred dosage of the therapeutic composition according to the present invention varies depending on factors such as the formulation method, administration method, the age, body weight and gender of the patient, severity of the disease, food, administration time, administration route, excretion rate and responsiveness of the patient. However, it can be suitably selected by a person skilled in the art.

However, in order to achieve therapeutic effects, an ordinarily skilled practitioner can easily determine and prescribe the dose effective for the desired treatment. For example, the therapeutic agent includes intravascular injection, subcutaneous fat injection, intramuscular injection, and direct injection into the ventricle or spinal cord using a microsyringe. Multiple injection and repeated administration are possible. In the case of intravascular injection, the effective dose of a vector per kg of body weight is 0.05 to 15 mg/kg, the effective dose of a recombinant virus is $1 \times 10^7$ to $1 \times 10^{11}$ virus particles ($1 \times 10^5$ to $1 \times 10^9$ IU)/kg, the effective dose of a cell is $1 \times 10^3$ to $1 \times 10^6$ cells/kg. Preferably, the effective dose of a vector is 0.1 to 10 mg/kg, the effective dose of a recombinant virus is $1 \times 10^8$ to $1 \times 10^{10}$ virus particles ($1\times10^6$ to $1\times10^8$ IU)/kg, the effective dose of a cell is $1\times10^2$ to $1\times10^5$ cells/kg. It can be administered 2 to 3 times a week. The dosage is not limited thereto and may vary depending on the condition of the patient and the severity of the neuronal disease. In the case of subcutaneous fat injection, intramuscular injection, and direct administration to the affected area, the effective dose is $1\times10^7$ to $1\times10^9$ recombinant virus particles administered 2 to 3 times a week at intervals of 10 cm. The dosage is not limited thereto and may vary depending on the condition of the patient and the severity of the neuronal disease.

More specifically, the pharmaceutical composition of the present invention comprises $1\times10^5$ to $1\times10^{15}$ PFU/mL of recombinant adeno-associated virus. It is generally preferable to inject $1\times10^{10}$ PFU every other day for 2 weeks. It may be given once a day or divided into several doses.

The pharmaceutical compositions of the present invention may be prepared into a unit dosage form or a form packaged in a multi-dose container by formulation using a pharmaceutically acceptable carrier and/or excipient according to a method that person skilled in the art to which the present invention pertains can easily carry out. Here, the formulation may be a solution, suspension or emulsion in an oil or aqueous medium, an extract, a powder, a granule, a tablet or a capsule. It may further comprise a dispersant or a stabilizer.

Although the pharmaceutical composition of the present invention can be used as a monotherapy, it may also be used in combination with common chemotherapy. This combination therapy may allow more effective treatment. Chemotherapeutic agents that may be used with the composition of the present invention include AChE inhibitors, glutamic acid inhibitors, Aricept, Exelon, Namenda, Razadyne[M1], levodapa, and riluzole.

REFERENCE DOCUMENTS

[1] Moss, R. B., et al., 2007, Hum Gene Ther 18: 726-732
[2] Wu, Z., et al., 2007, Mol Ther.; Sabatino, D. E., et al., 2007, Mol Ther 15: 1677-1685; Wiwanitkit, V., 2007, Hum Gene Ther 18: 89-92
[3] McPhee, S. W., et al., 2006, J Gene Med 8: 577-588
[4] Li, C. et al., Cancer gene therapy 12: 913-925; Hacker, U. T., et al., 2005, J Gene Med 7: 1429-1438.
[5] Puhlmann M. et al., Human Gene Therapy 10:649-657 (1999); Ridgeway, "Mammalian expression vectors," In: Vectors: A survey of molecular cloning vectors and their uses. Rodriguez and Denhardt, eds. Stoneham: Butterworth, 467-492(1988); Baichwal and Sugden, "Vectors for gene transfer derived from animal DNA viruses: Transient and stable expression of transferred genes," In: Kucherlapati R, ed. Gene transfer. New York: Plenum Press, 117-148(1986) and Coupar et al., Gene, 68:1-10 (1988)
[6] Wang G. et al., J. Clin. Invest. 104(11):R55-62(1999)
[7] Chamber R., et al., Proc. Natl. Acad. Sci USA 92:1411-1415(1995)
[8] Nicolau and Sene, Biochim. Biophys. Acta, 721:185-190(1982); and Nicolau et al., Methods Enzymol., 149: 157-176(1987)
[9] Capecchi, M. R., Cell, 22:479(1980); and Harlan and Weintraub, J. Cell Biol. 101:1094-1099(1985)
[10] Graham, F. L. et al., Virology, 52:456(1973); and Chen and Okayama, Mol. Cell. Biol. 7:2745-2752(1987)
[11] Neumann, E. et al., EMBO J., 1:841(1982); and Tur-Kaspa et al., Mol. Cell Biol., 6:716-718(1986)),
[12] Wong, T. K. et al., Gene, 10:87(1980); Nicolau and Sene, Biochim. Biophys. Acta, 721:185-190(1982); and Nicolau et al., Methods Enzymol., 149:157-176(1987)
[13] Gopal, Mol. Cell Biol., 5:1188-1190(1985)
[14] Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)

Hereinafter, the present invention will be described in detail by way of examples and the like. However, these examples can be modified into various other forms and the scope of the present invention is not construed as being limited by these examples.

Experimental Method

1. Preparation of AAV-DX2
A DX2 expression vector (pcDNA3.0) was excised by EcoRI/XhoI and introduced into the EcoRI/XhoI site of AAV-MCS vector (provided by KRcroGen; type2).
2. ALS Mouse Experiment
(1) DX2 Mouse/SOD Mouse
A hSOD1G93A transgenic mouse (B6SJL-Tg (SOD1*G93A)1Gur/J), in which glycine at the 93rd codon of the cytosol Cu/Zn superoxide dismutase is replaced with an alanine base pair, was purchased from Jackson Laboratory (Bar Harbor, Me., USA). All experimental animals were used according to the guidelines of the Institute of Laboratory Animals Resources (SNU-110517-3, Seoul National University, Korea). An AIMP-DX2 transgenic mouse (provided by the laboratory of Sung-Hoon Kim, Ph.D. of Seoul National University) was cross-mated with the SOD mouse. A F1 mouse was used to compare the total lifespan and the expression of other symptoms between SOD1 TG and DX2 TG.
(2) Injection of AAV-DX2 into SOD Mouse
AAV-DX2 and -GFP were injected into the spinal cord. The specific experimental procedure is as follows:
Tg mice were randomly divided into two groups: AAV-GFP injected control group and AAV-DX2 injected group. 13-week-old mice were anesthetized by intraperitoneal injection of avertin. The skin of the back of the mouse was cut vertically (cm), and then pedicel was snipped with scissors and laminectomy was performed from T2 to L3 to remove the lamina. 1 µL of an AAV mixture (containing virus) was injected into the exposed spinal cord at a rate of 0.5 µL per minute 5 times (a Hamilton syringe (5 µL Model 75 RN SYR) fitted with a 31 gauge needle and connected with an ultra-micro 4 pump and a stereotaxic device (World Precision Instruments, Sarasota, Fla., USA) was used). The injection was performed at 600 to 900 µm, and the needle was fixed to the target site for 1 minute before and after injection to prevent backflow.
3. Behavioral Test
After AAV was injected into the mice, 14-week-old mice were trained for 1 week on a rotarod treadmill (7650 Accelerating model, Ugo Basile Biological Research Apparatus, Comerio, Italy) and then a behavioral test was performed to monitor motor coordination ability. The time during which a mouse can withstand rotation at 10 rpm was measured daily. A representative value of each experiment was calculated using three experimental readings (the mice were weighed and tested daily, and each mouse was tested 3 times for each behavioral test).

4. PD Mouse Experiment

PD mice were injected stereotaxically with AAV-DX2. A more detailed experimental procedure is as follows: Mice were anesthetized with a mixture of ketamine:Rompun (3:1) and placed in a stereotaxic frame for skull perforation. During the perforation process, the head was continuously washed with a physiological saline solution to prevent the underlying cortex from overheating. 3 μl (200,000 cells/3 μl) of AAV-DX2 was injected into the left hemisphere striatum of a total of 70 mice at the following coordinates from bregma: AP+0.5 mm, ML±1.7 mm and DV −3.2 mm. The precipitate was fed by an infusion pump at 0.5 μl/min. After completion of injection, the needle was left for 5 minutes and then slowly removed.

5. Rotarod Test

Rotarod test is to evaluate the limb movement coordination function and sense of balance (exercise function) of animals. It was carried out in accordance with the following procedure:

An accelerating rotarod test was performed to observe whether the treated group mice exhibit dyskinesia. The animal was placed on a rolling rod at an initial speed of 4 rpm. Two tests were performed at an interval of 1 hour, and the tests were performed under severe speed conditions (4 to 40 rpm). The average time at which the mouse fell off the rotarod was recorded.

6. Pole Test

A method slightly modified from Matsuura's method was used. A vertical wood pole was wrapped with a tape to create rough surfaces. The animal head was placed on the top of the pole. The time to turn completely downward (T/turn) and the total time at which all of the four feet reach the floor (T/floor) were recorded. When the animal could not turn completely, the time to reach the floor was used as T/turn. Five tests were performed on each animal and the average score was used as the final pole test score.

7. Isolation of Primary Neurons

Primary neurons were isolated from the 18-day embryo (E18) or E19 of Wistar rats. Pregnant female Wistar rats were purchased from SLC (Shizuoka, Japan). Approximately 10 fetuses were obtained from each rat and the whole brain was separated from fetuses. The cortex was dissected from the brain using two pairs of fine tweezers and a stereoscopic microscope.

After dissection, it was carefully washed 3 times with 7 to 8 mL of phosphate buffered saline (PBS, Wako) in a 15-mL conical tube. After washing, 5 mL of papain solution and 20 to 60 mL of deoxyribonuclease I (DNase I, 5 units/mL, Takara, Shiga, Japan) were added to the cortex in the tube, followed by incubation at 32° C. for 12 minutes. The papain solution was prepared by dissolving 70 mg of papain (0.5 units/g, Wako) and 10 mg of ethylenediamine tetraacetic acid-2Na (Wako) in PBS to make a total of 20 mL. The papain solution was filtered through a 0.2-mm filter (Sartorius, Gottingen, Germany) and equally divided into 5 mL and stored at −30° C. The papain solution was slowly thawed at 4° C. several hours before use.

After incubation and digestion with the enzyme, the cortex was gently pipetted 12 times using a glass Pasteur pipette, filtered using a wet cell strainer (40-mm mesh, BD Biosciences), and placed in a 50-mL conical tube. The cell strainer was pre-wetted with 10 mL MEM (Sigma) containing 20% FBS (Gibco) and 1% N2 supplement (1006, Invitrogen, Life Technologies) to prevent non-specific neuron adhesion. The whole cortical suspension was poured through the cell strainer[M2], 10 mL of 20% FBS/N2/MEM was poured on top of it, and the neurons remaining on the filter paper were collected.

8. Measurement of Apoptosis Using FACS

N2A transfected with a plasmid encoding EV, AIMP2 or DX2 was cultured in the presence or absence of FasL or CHX/TNFα (30 ng/ml) for 24 or 12 hours, fixed in 70% ethanol at 4° C. for 1 hour, and washed twice with ice-cold PBS. Then, $1 \times 10^6$ cells were stained with propidium iodide (50 μg/ml) containing 0.1% sodium citrate, 0.3% NP-40 (nonylphenoxylpolyethoxylethanol 40) and 50 μg/ml of RNaseA for 40 minutes, followed by analysis with a flow cytometer (FACSCalibur, Becton-Dickinson). Sub-G1 cells were counted to measure dead cells. For each sample, 20,000 cells were analyzed using Cell Quest Pro software. All experiments were repeated 3 times.

N2A cells were transfected with SOD wt, SOD mutated at position 85 and SOD mutated at position 93, which are a representative gene known to cause ALS and mutants thereof. AIMP2 gene, which is known to promote apoptosis, was also introduced into one group of the cells, and DX2 gene, which is known to inhibit the apoptotic function of AIMP2, was introduced into the other group of the cells. Then, they were treated with FasL (20 ng/ml) for 24 hours to induce apoptosis. The result showed that, when AIMP2 was overexpressed, the mean apoptosis rate increased by about 8% for wt and about 15% for mutants, with significance ($p<0.01$). When DX2 was overexpressed, the apoptosis level was almost back to a level similar (with no significance) to the case where an empty vector (PcDNA3.0) was introduced.

This inhibition of N2A cell apoptosis by DX2 was similarly confirmed in the treatment with TNF-alpha, which is a typical inflammatory apoptosis-inducing factor, in addition to FasL. When the cells were treated with 10 μg/ml of cycloheximide (CHX, compound added to observe the apoptosis of TNF-alpha) and 30 ng/ml of TNF-alpha (mouse) for 12 hours, wt increased the apoptosis rate of about 20% and mutants exhibited the apoptosis rate of 40% or more. However, when DX2 was overexpressed, the apoptosis rate increased by only about 5% and 10% for the respective cases, inhibiting the apoptosis with significance ($p<0.01$ relative to EV control group). The y-axis represents the cell death % measured from FACS test.

9. MTT Analysis

Cell suspensions of N2A or primary neurons were seeded in a 96-well plate at a concentration of $5 \times 10^4$ cells per well. First, 3-(4,5-dimethylthiazol-2-yl)-2,5-diphenyltetrazolium bromide (MTT) was prepared as a stock solution (5 mg/mL in PBS, pH 7.2) and then filtered. 15 μL of MTT solution was then added to each well. After incubation at 37° C. under 5% $CO_2$ for 4 hours, 185 μL of solubilization solution/stop was added to each well. The 96-well plate was prepared for ELISA. Absorbance was measured at 620 nm to determine cell viability. The percent survival was calculated as the absorbance ratio of treated cells to untreated cells.

The inhibition of N2A apoptosis by DX2 was also confirmed in primary neurons. It was confirmed by infecting them with AAV-GFP or DX2 and treating them with FasL and CHX/TNF-alpha. In FasL, the apoptosis inhibition of about 4 to 5% based on GFP was observed with significance. In TNF-alpha, the apoptosis inhibition of about 5% was also observed. The results are expressed as a percentage of the control group.

Meanwhile, in order to induce oxidative stress, which is known to be a main cause of Parkinson's disease in primary neurons, the cells were treated with hydrogen peroxide (100

μM, 36 h) and then the apoptosis was determined by MTT analysis. The apoptosis inhibition of about 8% was observed with significance.

AIMP2-DX2 transgenic mice exhibited a prolonged lifespan and showed ameliorated dyskinesia in behavioral test, PD mouse experiment, rotarod test, and pole test, compared to the control mice.

Also, the present invention was found to significantly reduce neuronal apoptosis. Thus, the present invention can be usefully used as an active ingredient for preventing neuronal diseases, specifically Alzheimer's disease, Parkinson's disease, amyotrophic lateral sclerosis, mild cognitive impairment, multi-infarct dementia, frontotemporal dementia, dementia with Lewy bodies, Huntington's disease, neurodegenerative diseases, metabolic brain diseases, depression, epilepsy, multiple sclerosis, corticobasal degeneration, multiple system atrophy, progressive supranuclear palsy, dentatorubropallidoluysian atrophy, spinocerebella ataxia, primary lateral sclerosis, spinal muscular atrophy and stroke or for ameliorating, alleviating or treating symptoms resulting from the diseases.

While the present invention has been described with respect to the specific embodiments, it will be apparent to those skilled in the art that various changes and modifications may be made without departing from the spirit and scope of the invention as defined in the following claims.

What is claimed is:

1. A method for improving motor activity or prolonging lifespan of a subject with amyotrophic lateral sclerosis (ALS), comprising administering to the spinal cord of the subject a pharmaceutically effective amount of a viral vector comprising an exon 2-deleted AIMP2 variant (AIMP2-DX2) gene.

2. The method according to claim 1, wherein the exon 2-deleted AIMP2 variant (AIMP2-DX2) gene has a base sequence set forth in SEQ ID NO: 1.

3. The method according to claim 1, wherein the viral vector is selected from the group consisting of adeno-associated virus (AAV), adenovirus, lentivirus, retrovirus, vaccinia virus, and herpes simplex virus.

4. A method for reducing or ameliorating dyskinesia in a subject with Parkinson's disease (PD), comprising administering to the brain of the subject a pharmaceutically effective amount of a viral vector comprising an exon 2-deleted variant (AIMP2-DX2) gene.

5. The method according to claim 4, wherein the exon 2-deleted AIMP2 variant (AIMP2-DX2) gene has a base sequence set forth in SEQ ID NO: 1.

6. The method according to claim 4, wherein the viral vector is selected from the group consisting of adeno-associated virus (AAV), adenovirus, lentivirus, retrovirus, vaccinia virus, and herpes simplex virus.

7. The method according to claim 4, wherein the administering to the brain is by stereotaxic injection.

8. The method of claim 1, further comprising administering to the subject a therapeutic agent.

9. The method of claim 4, further comprising administering to the subject a therapeutic agent.

* * * * *